United States Patent
Torrens

(10) Patent No.: US 6,179,800 B1
(45) Date of Patent: Jan. 30, 2001

(54) SPLINT

(75) Inventor: George E. Torrens, Uxbridge (GB)

(73) Assignee: Brunel University, Middlesex (GB)

( * ) Notice: Under 35 U.S.C. 154(b), the term of this patent shall be extended for 0 days.

(21) Appl. No.: 08/750,310

(22) PCT Filed: Jun. 8, 1995

(86) PCT No.: PCT/GB95/01340

§ 371 Date: Mar. 5, 1997

§ 102(e) Date: Mar. 5, 1997

(87) PCT Pub. No.: WO95/33428

PCT Pub. Date: Dec. 14, 1995

(30) Foreign Application Priority Data

Jun. 8, 1994 (GB) .................................................. 9411445

(51) Int. Cl.[7] .................................. A61F 5/00; A61F 5/37
(52) U.S. Cl. .................................. 602/21; 602/5; 128/878
(58) Field of Search .................................. 602/5, 12, 13, 602/20, 21, 23, 32, 39, 60, 62; 128/878–879, 877, 882, DIG. 20

(56) References Cited

U.S. PATENT DOCUMENTS

| | | | |
|---|---|---|---|
| 661,812 | * 11/1900 | McKown et al. | 602/39 |
| 2,079,567 | * 5/1937 | Anderson | 602/39 |
| 2,312,523 | * 3/1943 | Corbett | 602/21 |
| 2,318,864 | * 5/1943 | Jackson | 602/21 |
| 2,682,869 | * 7/1954 | Papp | 602/21 |
| 2,692,594 | * 10/1954 | Kelly | 602/21 |
| 2,744,526 | * 5/1956 | Saylors | 128/878 X |
| 2,767,708 | * 10/1956 | Keropian | 602/21 |
| 2,863,449 | * 12/1958 | Spencer | 602/21 |
| 3,423,095 | * 1/1969 | Cox | 128/878 X |
| 3,707,963 | * 1/1973 | Keropian | 602/21 |
| 4,378,009 | * 3/1983 | Rowley et al. | 128/20 X |
| 4,436,088 | * 3/1984 | Finnieston | 602/20 |
| 4,790,300 | * 12/1988 | Marx | 602/21 |
| 4,873,968 | * 10/1989 | Finnieston et al. | 602/21 |
| 4,966,137 | * 10/1990 | Davini | 602/21 |
| 5,171,310 | * 12/1992 | Chisena | 602/20 X |
| 5,203,766 | * 4/1993 | Carter et al. | 602/21 |
| 5,286,249 | * 2/1994 | Thibodaux | 602/20 X |
| 5,295,951 | * 3/1994 | Fareed | 602/20 X |
| 5,383,844 | * 1/1995 | Munoz et al. | 602/20 |
| 5,468,220 | * 11/1995 | Sucher | 602/21 |
| 5,520,625 | * 5/1996 | Malewicz | 602/21 |
| 5,944,677 | * 8/1999 | Richard | 602/23 |

FOREIGN PATENT DOCUMENTS

590664 * 8/1977 (CH) .................................................. 602/21

* cited by examiner

*Primary Examiner*—Mickey Yu
*Assistant Examiner*—Denise Pothier
(74) *Attorney, Agent, or Firm*—Craig A. Fieschko, Esq.; DeWitt Ross & Stevens S.C.

(57) ABSTRACT

A splint (17) includes first and second collars (18,19) pivotally supported on a body member (20) and adjustable so as to adjust the internal dimensions of the splint (17). A plurality of spaced resilient pads (21–27) are provided on the internal surfaces of the splint (17) so as to exert pressure on a limb (11) held in the splint (17) while allowing vascular flow. The splint (17) is provided with a support (36) for supporting the extremity of a limb, such as a hand (14) or foot. The support (36) allows some movement of the limb extremity to reduce swelling by promoting vascular flow.

20 Claims, 5 Drawing Sheets

SPLINT

BACKGROUND OF THE INVENTION

The present invention relates to a splint for a fractured limb and in particular to a more efficient method of holding a fractured limb, such as a wrist, in reduction. The most common used method of maintaining reduction of a stable Colles' Fracture is by the use of a plaster cast. It is inexpensive and can be efficiently applied to the patient's limb. However, it does not offer any indication to the clinician applying the cast of the intra-cast pressures that may lead to compartment syndrome. Once the cast is set it is difficult to adjust. If the clinician then finds the fracture site is misaligned the cast must be redone. There is no easily made adjustment that allows loosening to accommodate swelling of the forearm and wrist, or tightening of the cast as the swelling reduces.

BRIEF SUMMARY OF THE INVENTION

The proposed preferred method of maintaining of Colles' fracture, a specific type of fracture, involves the use of a modular adjustable outer casing. This casing has a locking mechanism which can easily be adjusted by the clinician, but tamperproof by the patient. The adjustment is in small steps to allow objective recording of the splint settings. There are preferably three sizes of casing, covering a similar anthropometric range to that of functional bracing commercially available. The common incidence of Colles' fracture across the population is a further factor in detailing the splint dimensions. The internal contours of the casing are designed so as to avoid creating a complete collar around the limb. This feature gives a path for the flow of fluid from the trauma site, avoiding pressure build up.

BRIEF SUMMARY OF THE INVENTION

There is also preferred stepped adjustment of the hand support in the lateral and median planes. This support incorporates some adjustment to allow limited movement of the hand in palmar flexion, but not dorsiflexion, and lateral movement in both adduction and abduction. The flexibility of cast positioning gives the clinician more options to balance the maintenance of reduction of the fracture components and allowing movement of the forearm and hand promoting muscle tone. It can also reduce swelling conventionally occurring with Colles' fractures by promoting vascular flow induced by hand movement.

Plaster casting is recognized as providing poor maintenance of reduction. Other treatments, such as external and internal fixation, pose other post-reduction problems especially in relation to the elderly who may have poor bone structure due to Osteoporosis which does not provide a suitable site to hold the fixtures.

GB-A-2,156,226 discloses a fracture splint, suitable for example for trochanteric fractures, comprising an adjustable girdle for locating it on the patient's body, the girdle supporting an elongate member including means for restraining limb movement and incorporating an anchorage enabling pressure to be applied to the fracture area. The girdle may comprise two adjustably interconnected, molded segments engageable with the patients iliac crest, one segment supporting anchorage points for straps, the tension in which urges a pressure pad against the fracture area, and the other segment having mounted on it a semi-rigid rod supporting along its length the pressure pad, a knee retainer and a foot clamp.

According to an aspect of the present invention, there is provided a splint for supporting a fractured limb comprising a rigid outer casing including a plurality of spaced pressure sites located at the inner surfaces of the casing and operative to apply pressure to a limb to be supported while retaining a vascular flow path; longitudinally spaced proximal and distal collars, each provided with one or more pressure sites, said proximal and distal collars being spaced so as to envelop a common bone of the limb and being independently adjustable relative to one another so as to provide independent adjustment of the internal dimensions of the casing. This splint can be designed so as not to hinder tendon function and to allow space for free vascular flow, which can reduce swelling. It can also reduce reflex sympathetic dystrophy, nerve entrapment and compartment syndrome. The proximal and distal collars can provide visual access to the limb.

The pressure sites are preferably provided by resilient pressure pads located on the inner surface or surfaces of the casing. Each pressure pad can be individually chosen or adjusted to provide the appropriate individual pressure for its particular point of application. For example, some points of the limb may benefit from more pressure than others and vice versa. This is not possible with a conventional cast.

In the preferred embodiment, the splint comprises means to support the limb so as to allow limited movement of the limb extremity or extremities. The term extremity is intended to include a hand or foot or the like. Allowing movement of these body segments can reduce swelling commonly occurring with Colles' fractures by promoting vascular flow through movement of the extremity.

The splint may include pressure sensing means for sensing pressure exerted on one or more of the pressure sites. The pressure sensing means may be incorporated in one or more pressure pads.

In one embodiment, the pressure sites are adjustable in dependence upon the sensed pressure to adjust the pressure produced thereby.

According to another aspect of the present invention, there is provided a splint for a fractured limb comprising longitudinally-spaced proximal and distal collars and means for supporting a hand, foot or other body segment in relation to another as appropriate at the side of the distal collar remote from the proximal collar.

In preferred arrangements the collars are individually adjustable; in addition there are rigid interconnections between the collars and between the distal collar and the hand, foot or other body segment support.

According to another aspect of the present invention there is provided a splint for a fractured limb comprising at least one collar, the collar comprising an internal pad or cell, and means for sensing the pressure exerted on said pad or cell.

Preferably there are at least two collars and each collar has a plurality of pressure sensing means. In the light of the pressure sensed, the size of the collars and/or the pressure applied by said pads or cells may be individually adjusted.

According to another aspect of the present invention there is provided a method of adjusting a splint in accordance with the second aspect wherein the adjustment is made in dependence upon the sensed pressures. This method may be used during development of a splint, to determine the pressure to be applied at the various pressure sites. Subsequent splints may then omit any pressure sensing means.

Preferred embodiments may have one or more of the following features:

A rigid outer casing which is adjustable by a measured amount to accommodate a variation in dimensions within a section of the anthropometric range of the population.

A number of standard component sections which may be added to for specific holding positions after treatment. These sections may be removed as part of rehabilitation therapy.

One or more axes of adjustment dependent upon the holding position required.

A measurable adjustment achieved through the use of a spigot locating within a number of recess options available. This will result in a change in dimension of the splint by a known amount. This allows objective records to be kept of treatment given to a patient.

An outer casing which can be adjusted and a pressure indicator/alarm which can be reset without removal or replacement of the splint.

Incorporated within the outer casing are a number of pressure indicators. These are located where the holding pressures will be applied to the fracture site and the surrounding areas where the splint is supported on the body. The pressure indicator may comprise a small electronic pressure sensor, a mechanical diaphragm, or a reservoir with liquid which above a specified pressure, transfers to another container where it can be seen, or any other appropriate sensing or indicating device.

The indicator will also act as a warning alarm to the patient or clinician that excessive pressure has built up at the splint-body interface. The patient can then seek medical assistance to adjust the splint. The alarm may be given by an audible/visible or a vibratory method, or by a combination of these.

The splint will be made of materials that will allow x-rays to be taken with the splint in place.

Splints in accordance with the present invention may be based on the use of a modular outer casing and an option for the inner wall to be customized to the forearm or any other limb or body part using mechanical adjustable of the circumference of the splint collars or using air cells which can be inflated or deflated to take up the space between the outer casing and the body. The valve through which the air cell is inflated/deflated may also fasten the air cell in position within the casing of the splint.

Previous studies into plaster casting techniques for Colles' fracture show a potential for excessive pressure to build up within conventional plaster casts leading to compartmental syndrome. Plaster casts have a limited ability to be adjusted once set. The clinician relies heavily on experience to feel the cast wall is applying the correct pressure, and is in the correct position. There is a lack of objective information available to the clinician when applying the splint to maintain reduction. A commercially available system which incorporated such feedback has not yet been found.

BRIEF DESCRIPTION OF THE DRAWINGS

An earlier splint for Colles' fracture of the wrist that incorporated a pressure interface is known as the Aberdeen Brace. This system of splinting produces localized high interface pressures. It comprises a commercially available functional brace modified to accept monitoring components. The flexibility of the splint wall and a lack of a hand support contributes to the high intra-cast pressures.

The hand support of the present invention when applied to Colles' fracture of the wrist was found to reduce the forces applied to the forearm and wrist necessary to hold the position of the splint over the fracture site using the hand support as a locator and to reduce the effectiveness of forces generated by the muscles of the forearm that may cause misalignment.

Plaster casting is still the most popular method of maintaining reduction of Colles' fracture. Yet it has been acknowledged that this method is limited in its usefulness. There are commercially available air splints for use in emergency situations, which apply a uniform pressure over the whole forearm. These are not designed to maintain a holding pressure on specific areas of the forearm over a six week period. Thermoformed splinting materials are difficult to apply to Colles' fracture due to the heat of the material on the patient and the short manipulation time before the material cools and stiffens. It then requires reheating.

Preferred embodiments of the present invention as applied to Colles' fracture of the wrist will now be described, by way of example only, with reference to the accompanying drawings, of which:

DETAILED DESCRIPTION OF THE INVENTION

Figure 1:
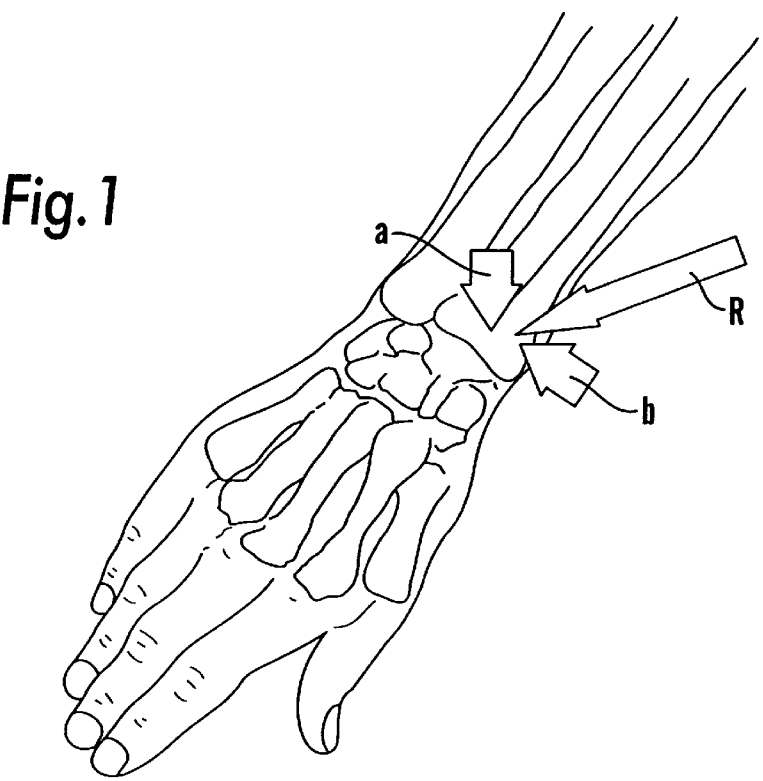
Figure 2A:
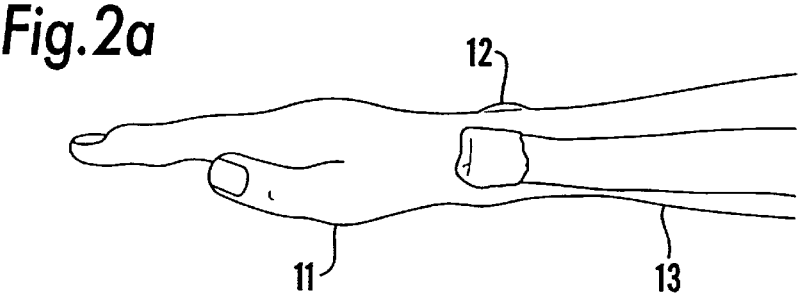
Figure 2B:
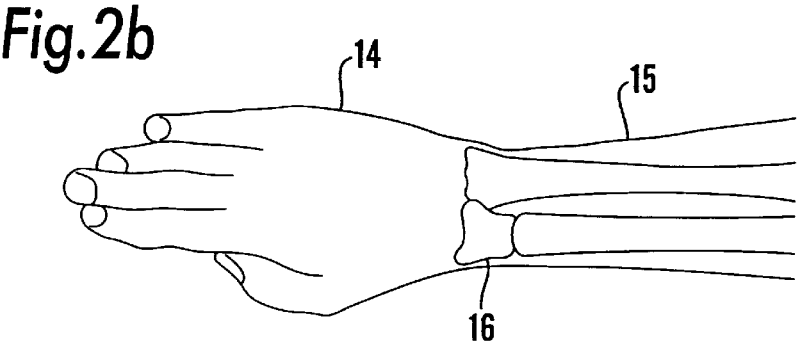
Figure 3A:
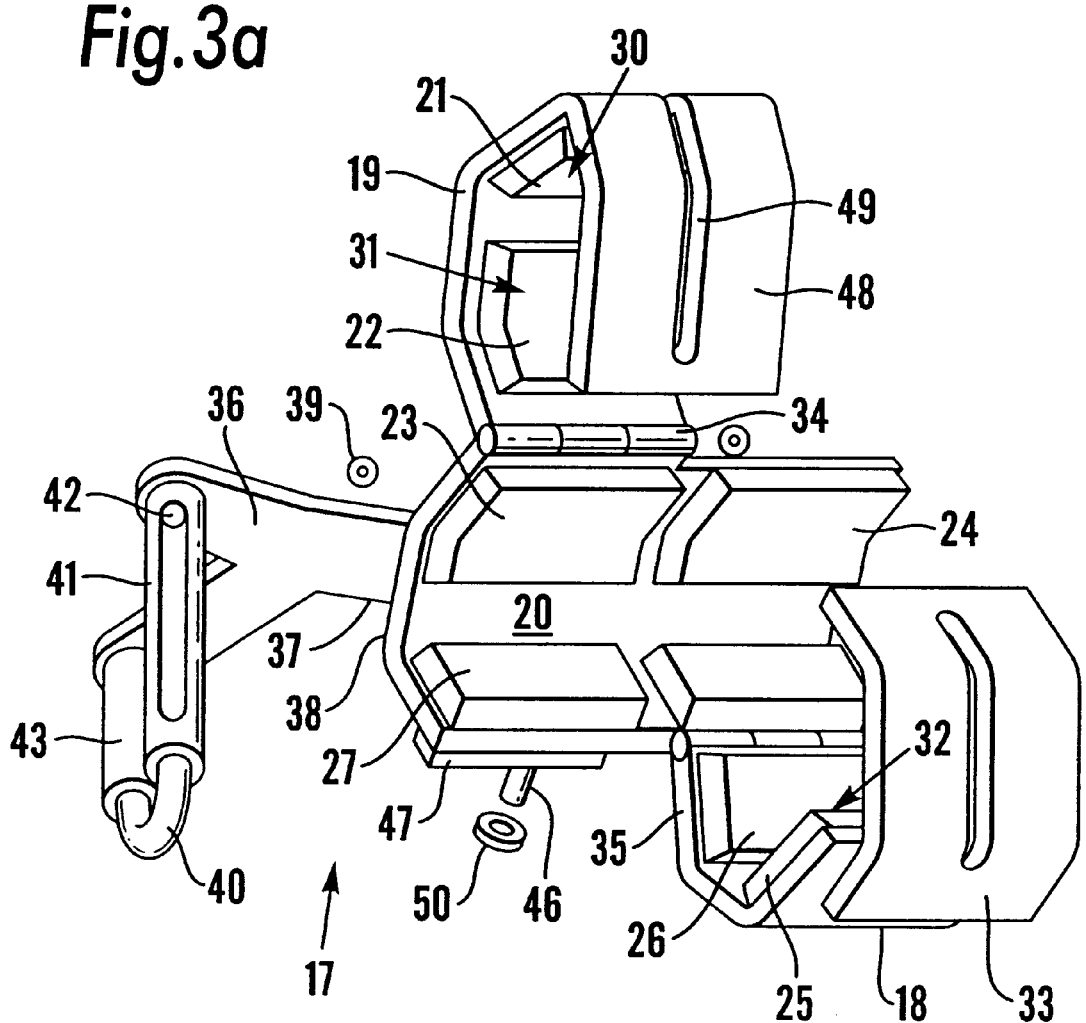
Figure 3B:
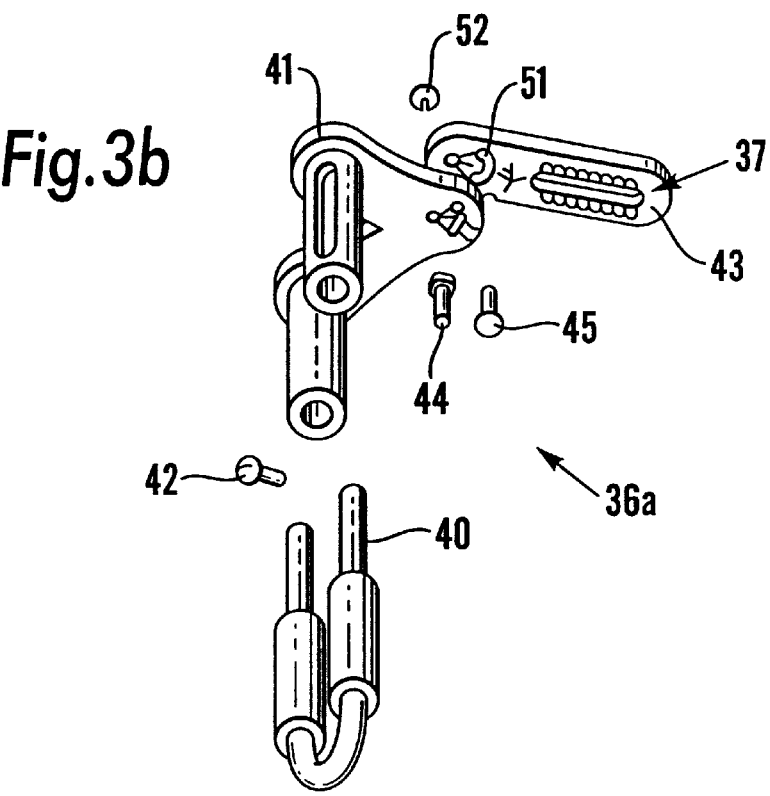
Figure 4:
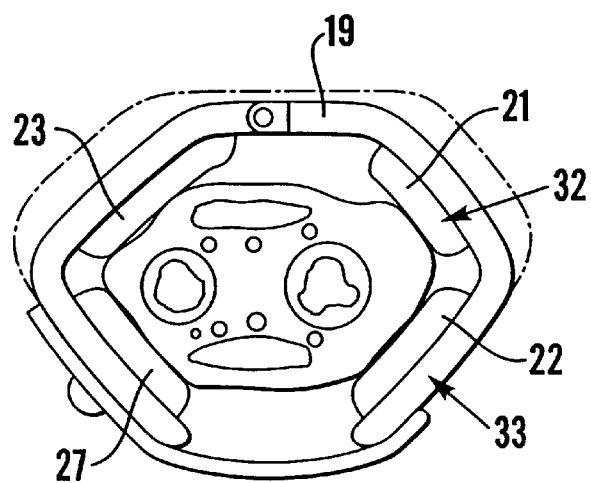

FIG. 1 shows the forces necessary to maintain reduction of a Colles' fracture of the wrist;

FIGS. 2a and 2b indicate the locations of the applied holding pressures necessary on two perpendicular axes;

FIGS. 3a and 3b show a splint in accordance with a first embodiment of the present invention;

FIG. 4 shows a cross section of the splint of FIG. 3.

Figure 5:
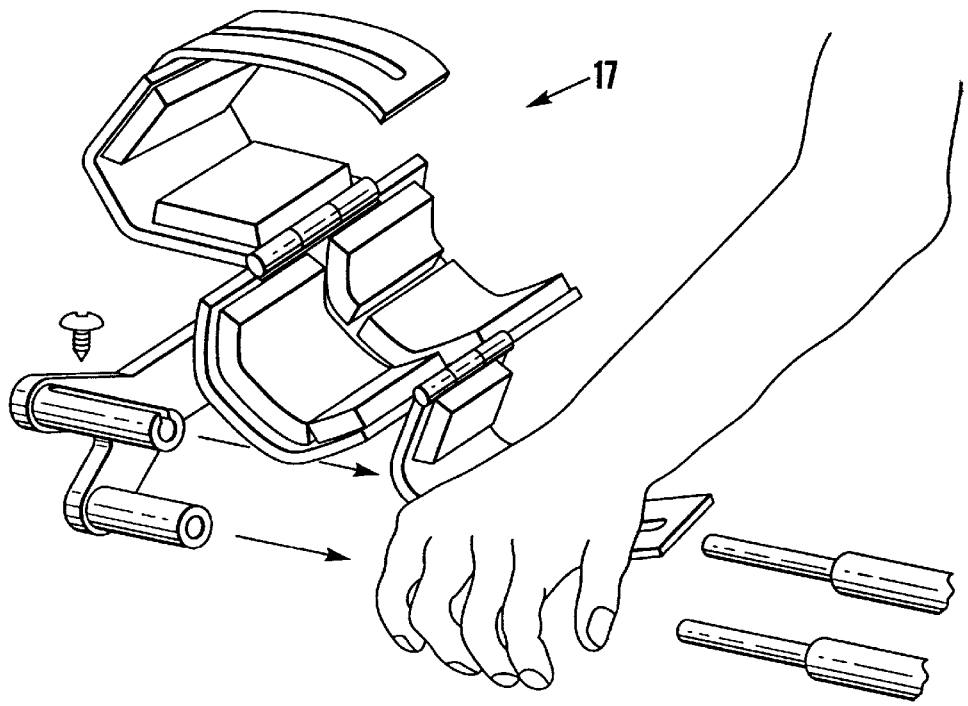
Figure 6:
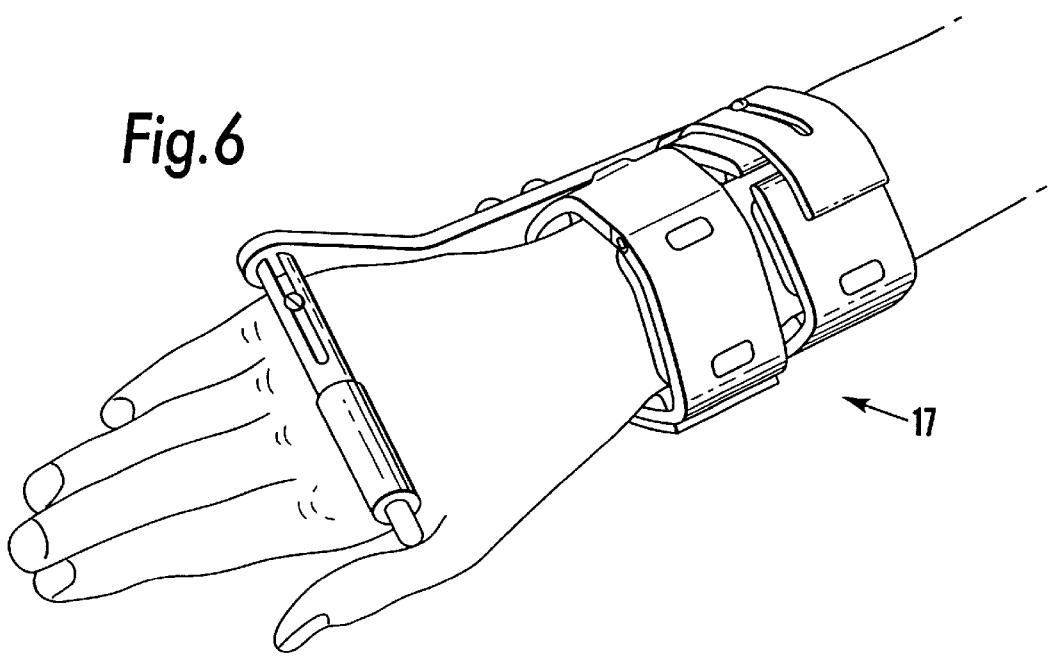
Figure 7:
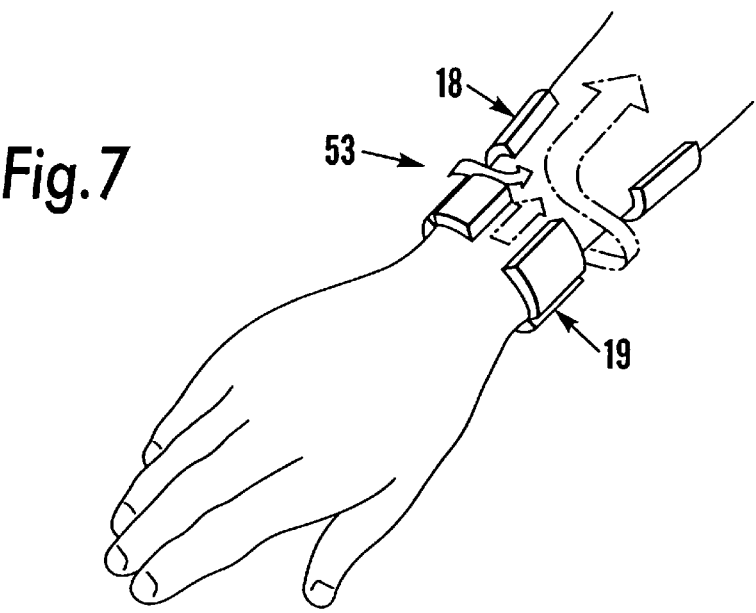
Figure 8:
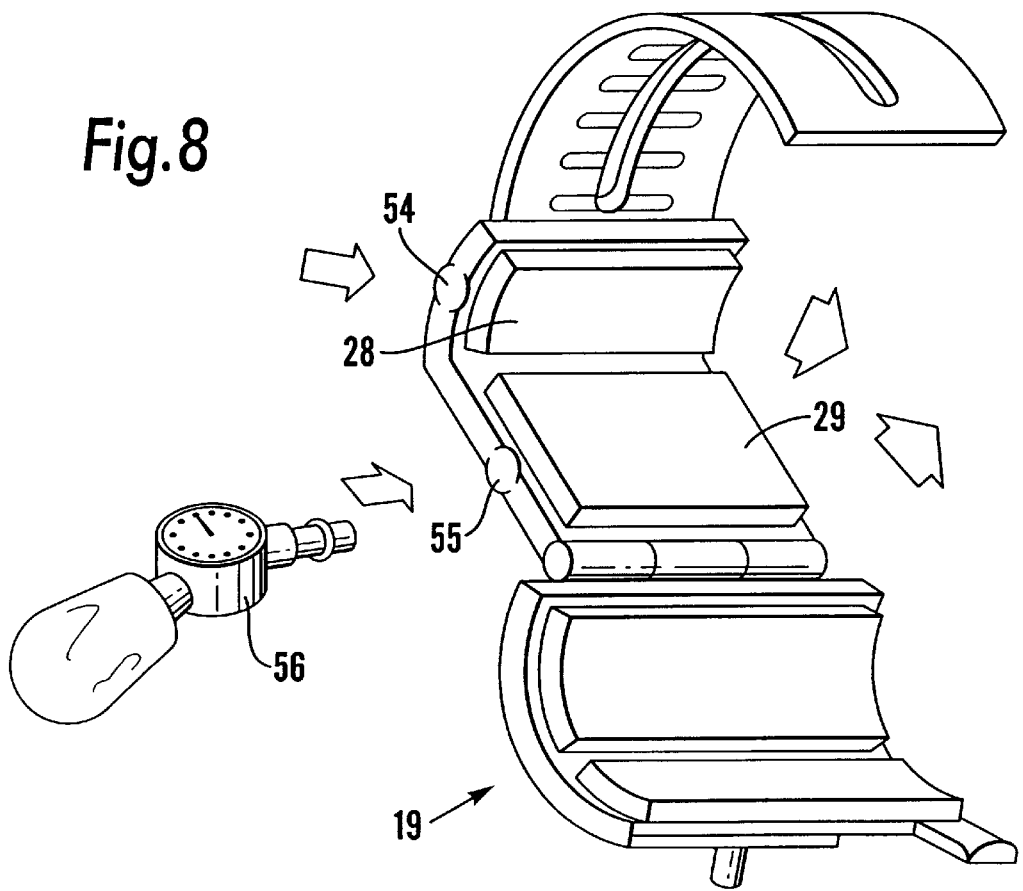

FIG. 5 shows a splint of FIG. 3 about to be applied to a wrist;

FIG. 6 shows a splint of FIG. 3 in its closed configuration applied to a patients arm;

FIG. 7 shows a schematic view of the splint of FIG. 3 with various parts omitted to show the flow of blood; and FIG. 8 shows a splint in accordance with a second embodiment of the present invention.

Colles' fracture is diagnosed as occurring 25 mm from the distal end of the radial bone. The vectorial components a, and b, resulting in the holding force R, that are required to maintain reduction of the fracture are shown in FIG. 1. The three point loading technique used to apply the holding pressure at points 11 to 16 are shown in FIGS. 2a and 2b.

A first embodiment of the present invention is shown in FIG. 3. A splint 17 comprising two collars 18 and 19 made of engineering plastic and a main body 20. These are contoured to apply pressure at the predetermined positions only via closed cell foam pads 21 to 27 or alternatively via air cells which are adjustable in pressure 54 and 55 as shown in FIG. 8. The pressure indicators 30 to 33 are used to warn the patient and clinician when excessive intra-cast pressures occur during application of the splint and during use. The two collars are connected to the main body 20 that locates along the axis of the distal end of the ulna bone of the forearm. The two collars pivot at the attachment point to the main body on two flat hinges 34 and 35.

A second feature relating to the pressure sensing indicator/alarm and their location within the collars of the splint is shown in FIG. 4. The positions of the sensors/pads of the splint in position are shown in cross-section on the distal collar and defined as follows.

The pressure sensors 30 and 31 are incorporated into the rigid outer casing of the collar 19 under the closed cell foam pads 21 and 22. The position and configuration of the pads in relation to the wrist and forearm provide the holding force in the directions of a and b shown in FIG. 1. Opposing the applied force from the pads 21, 22 on collar 19 are pads 23, 27 set opposite and are attached to the main body of the splint 20. The range of adjustment within the collar around the hinge does not affect the positioning of the pads enough to require repositioning of them. The holding pressure is applied to the bone fragment and the proximal shaft of the radial bone. The configuration of the pads 24, 25, 26 and integral sensors 32, 33 is repeated in the proximal collar 18. When a predetermined safe pressure threshold has been exceeded the sensor will trigger an alarm. The alarm may be visible, audible or vibration or a combination of two or more. The alarm and pressure sensor may be integral in the form of a diaphragm which is moved to allow a peg to be visible above the surface of the casing, or a colored liquid reservoir that is compressed forcing the liquid into a restricted tube which passes the outer surface of the casing where it can be seen. Alternatively, the alarm and sensor may be separate in the form of a strain gauge and miniature loudspeaker with a microprocessor that would be powered by a watch battery.

The pads 21 and 22 are 37 mm×40 mm long and apply a holding pressure that overlaps the fragment and shaft giving support to the realignment of the bone. The pads avoid applying pressure over the medial, radial or ulna nerve which pass through the wrist. Application of pressure over the dorsal and volar aspects of the forearm is kept to a minimum to allow free movement of the tendons promoting early mobilization of the hand and digits. Fluid can drain back into the body from the fracture site through areas where pressure is not applied as shown in FIG. 7. The two collars are separated by a 15 mm gap 53. The positioning of holding pressures on to the forearm in different axial planes avoids isolating sections of the circulatory system. The gap allows fluid flow between the pressure zones of the two collars 18 and 19.

If a hand support is not used it is envisaged the proximal pads would need to exert a greater holding pressure on to the forearm to maintain stability of position. It would also be advantageous to maintain a three point loading on the fracture site. As the proximal forearm is not so badly affected by the fracture there are more options for the positioning of the holding pressure.

The range of travel within the casing had been determined from the previously mentioned anthropometric and commercial information. It was determined a 10 mm change in diameter of the splint collars was necessary to cover the variation of wrist dimensions across the proposed three sizes of splint casing.

An alternative to the preferred pad and sensor configuration is the use of air cells as sensors and adjustment FIG. 8. The air cells 28 and 29 replace the foam pads and sensors within the proximal collar, shown in FIG. 8, and the distal collar of the splint. Valves 54, 55 are used to inflate and deflate the bellows arrangement of the individual cells to fill the gap between the casing and the forearm/wrist. The air will be inserted through a hand pump that may have an integral pressure indicator 56. When pressure is applied to the cell that exceeds the safe threshold an alarm will be triggered that is audible, visual or vibratory or any suitable combination.

A third feature, shown in FIG. 3a, is the adjustment of the collars 18 and 19. The spigot for the distal collar 46 and two ridges on either side at 47 are part of the main body 20. The collar 19 has measured grooves 49 in the tongue 48 that overlaps the main body and spigot. Once the collar circumference has been set by the clinician the collar can be fixed in position using a tamperproof nut 50. This configuration is repeated on the proximal collar 18.

There is a detachable hand support 36 that limits movement in palmar and dorsiflexion, ulna and radial deviation. The hand support does not immobilize the hand completely. It allows a few millimeters of movement in all directions to avoid joint stiffness and to promote vascular flow. The support is adjustable laterally along the axis of the forearm using the same configuration of a locating spigot 38 on the main body of the splint into indentations at measured intervals on the hand support 37. The support locked into position using a tamperproof nut 39.

The cross bar support 40 is adjustable to accommodate varying hand widths when the hand support 36 is being set by the clinician. The cross bar 40 sleeve onto the main hand support section 41 and is fixed in position using a tamperproof screw 42. The bar is covered in an inert closed cell foam 43 that helps to distribute the support load over a larger area just behind the metacarpophalangeal joints of the fingers. Where the thumb joins the hand, at the carpometacarpal joint, this area is used to locate the cross bar 40 and so avoid slippage of the splint along the axis of the forearm which would cause the splint to give an inappropriate support to the fracture site.

The hand support has an option to allow adjustment to the fixed holding angle of the hand 36a. The main hand support would have the lateral adjustment bar 43 and the cross bar support 41. The cross bar support will pivot on pin 44 and use grooves 51 and a spigot to give measured angular adjustment that is locked by a screw 45 and a tamperproof nut 52.

FIGS. 5 and 6 show splint 20 that is preferably applied as follows:

1. The uninjured forearm/wrist is used to gauge which of the three sizes of brace or splint 20 will be fitted.

2. The hand support 36 with the correct degree of palmar flexion/ulna deviation pre-set is attached to the brace making sure the cross bar 40, 41 lies just behind the metacarpophalangeal joints of the fingers.

3. Manipulation and reduction is carried out by the doctor.

4. The underlying stockinette is applied to the forearm.

5. The splint/brace 20 is applied whilst the forearm is held in reduction.

6. The hand is located into the cross bar 41, which can be adjusted to fit different hand widths and thicknesses.

7. The proximal collar 18 is then closed around the arm until the collar "feels" to be at the correct pressure, and fastened together with the nut provided.

8. The above sequence is repeated with the distal collar 19.

9. Alternatively if the air cells 28, 29 are used the proximal and distal collars could be set close to the forearm/wrist. A pressure evaluation as made by Talley Ltd. 59 could be used to inflate the air cells to a pre-set pressure which would be achieved once the space had been filled between the casing and the forearm/wrist.

10. The radial bone is then checked to ensure reduction is being maintained properly.

11. The splint position and pressures are reviewed.

12. All nuts are tightened and locked.

Although the above-described modular splints are similar in weight to a plaster cast, and initially more expensive the benefits will be as follows:

Less incidence of compartment syndrome by the use of the intra-cast pressure monitor/alarm. This avoids surgery to restore some function to the hand when the median nerve is damaged through blood occlusion.

Patients can have an indicator that tells them when high pressures are occurring, and to return to the hospital. Less incidence of misalignment of the distal fragment and the proximal shaft of the radius. This may involve surgery to reset the original fracture where function of the hand has been severely affected.

Objective information may be available to the clinician during application of the splint. This should help less experienced staff apply the splint more accurately.

Records can be kept of the splint settings. This information will be useful to the clinician if complications arise after treatment. Adjustments to the splint can then be more objectively monitored and evaluated as part of assessment of the efficiency of the treatment.

The casing can be adjusted easily if the condition of the trauma site changes. An increase, or decrease in swelling will affect the compartment pressure and the holding pressure applied to hand and forearm.

Adjustment of the hand support allows an appropriate amount of movement to the hand.

The time taken to apply and monitor the splint and that taken using plaster treatment is similar. The skill of the clinician is enhanced by the objective feedback from the interface pressure indicator providing more considered treatment.

Physiotherapy time is also reduced due to improved function post-cast. The large potential market allows mass production techniques to be used to produce the finished product. This should bring the cost of the splint to within the cost of functional bracing, normally used post-cast.

The use of a hand support reduces the hand's ability to produce a force against the splint. It also acts as a locator for the splint casing onto the forearm/wrist.

Various modifications may be made to the above-described splints. They may comprise only a single collar or more than two collars. They may be designed for the upper arm in which case the hand support may be omitted. They may be modified to be applied to a leg or ankle with or without an appropriate foot support. They may also be modified for the limbs of animals.

The disclosures in U.K. patent application no. 94/11445.1, from which this application claims priority, and in the abstract accompanying this application are incorporated herein by reference.

What is claimed is:

1. A splint for supporting a fractured limb comprising:
   a. a rigid outer casing including a substantially inflexible main body section having a concave inner surface extending between longitudinally spaced substantially inflexible proximal and distal collars which each have a concave inner surface, said proximal and distal collars being proximate to one another so as to circumferentially envelop a common bone of the limb between the collars and the main body section when in use, the proximal and distal collars being independently adjustable relative to one another so as to provide independent adjustment of the internal dimensions of the casing;
   b. a plurality of spaced pressure sites located at the inner surfaces of the main body section and the proximal and distal collars, the spaced pressure sites being operative to apply pressure to a limb to be supported while retaining a vascular flow path.

2. A splint according to claim 1, wherein the pressure sites are provided with a plurality of resilient pressure pads spaced about the inner surfaces of the main body section and collars, and wherein the casing only applies pressure to a limb situated when in use.

3. A splint according to claim 1, comprising means for supporting an extremity of the limb so as to allow limited movement of said limb extremity.

4. A splint according to claim 3, wherein the extremity support means includes a support structure extending beyond the casing, the support structure including a passage defined therein into when in use and first and second stops positioned in at least substantially parallel relation on either side of the passage.

5. A splint according to claim 4, wherein the stops are adjustable relative to one another for adjusting the size of the passage.

6. A splint according to claim 1, comprising pressure sensing means for sensing a continuous range of pressures exerted on one or more of the pressure sites.

7. A splint according to claim 6, wherein the pressure sensing means is incorporated in one or more pressure pads.

8. A splint according to claim 6, wherein the pressure sites are adjustable in dependence upon the sensed pressure to adjust the pressure produced thereby.

9. A splint according to claim 1 wherein each collar is provided with two or more of the pressure sites.

10. A splint according to claim 9 wherein each collar's pressure sites are spaced about the curve of each collar's inner surface.

11. A splint according to claim 1 wherein the pressure sites are adjustable independently of the collars to allow variation of pressure to a desired level.

12. A splint for supporting a fractured limb comprising:
   a. longitudinally spaced substantially inflexible proximal and distal collars situated adjacently so as to envelop a common bone of the limb when in use, the collars having concave inner surfaces,
      wherein the collars are independently adjustable,
      and further wherein the collars share a substantially inflexible concave main body section extending between the collars;
   b. a plurality of spaced pressure sites situated about the curves of the inner surfaces of the collars and on the main body section, the pressure sites being operative to apply pressure to a limb to be supported while maintaining a vascular flow path when in use.

13. A splint according to claim 12, comprising means to support an extremity of the limb so as to allow limited movement of said limb extremity.

14. A splint according to claim 13, wherein the extremity support means includes a support structure extending beyond the collars, the support structure including a passage defined therein into when in use.

15. A splint according to claim 12, comprising pressure sensing means for sensing a continuous range of pressures exerted on one or more of the pressure sites.

16. A splint according to claim 12 wherein the pressure sites are adjustable independently of the collars to allow variation of pressure to a desired level.

17. A splint according to claim 12 wherein the main body section includes multiple pressure sites.

18. A splint according to claim 1 wherein at least some of the pressure sites on the main body section are spaced about the curve of the main body section's inner surface.

19. A splint according to claim 1 wherein at least some of the pressure sites on the main body section are spaced between the collars.

20. A splint for supporting a fractured limb comprising:
a. a rigid outer casing including a substantially inflexible concave main body section extending between longitudinally spaced substantially inflexible concave proximal and distal collars, said proximal and distal collars being proximate to one another so as to circumferentially envelop a common bone of the limb between the collars when in use, the proximal and distal collars being independently adjustable relative to one another so as to provide independent adjustment of the internal dimensions of the casing;

b. wherein the main body, the proximal collar, and the distal collar each have an inner surface whereupon a plurality of spaced pressure sites are located, the when in use to apply pressure to a limb to be supported while retaining a vascular flow path.

* * * * *